US008377459B2

(12) United States Patent
Deckner et al.

(10) Patent No.: US 8,377,459 B2
(45) Date of Patent: Feb. 19, 2013

(54) COMPOSITION FOR WET WIPES THAT ENHANCES THE EFFICACY OF CLEANSING WHILE BEING GENTLE TO THE SKIN

(75) Inventors: George Endel Deckner, Cincinnati, OH (US); Lee Ellen Drechsler, Cincinnati, OH (US); Mathias Kurt Herrlein, Hofheim (DE); Ursula Christina Glaser, Wiesbaden (DE); Randall Glenn Marsh, West Chester, OH (US); Antonio Martinez-Campoy, Rüsselshiem (DE); Philip Andrew Sawin, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 771 days.

(21) Appl. No.: 10/883,314

(22) Filed: Jul. 1, 2004

(65) Prior Publication Data
US 2005/0008681 A1    Jan. 13, 2005

Related U.S. Application Data

(60) Provisional application No. 60/520,031, filed on Nov. 14, 2003, provisional application No. 60/485,848, filed on Jul. 9, 2003.

(51) Int. Cl.
*A01N 25/34* (2006.01)
*A61K 8/00* (2006.01)
(52) U.S. Cl. ......... 424/404; 424/401; 514/159; 510/130
(58) Field of Classification Search ................. 424/402, 424/401, 404
See application file for complete search history.

(56) References Cited

U.S. PATENT DOCUMENTS

| 4,379,755 | A |   | 4/1983  | Yamada et al.     |         |
|-----------|---|---|---------|-------------------|---------|
| 4,380,503 | A |   | 4/1983  | Koerner et al.    |         |
| 4,606,913 | A |   | 8/1986  | Aronson et al.    |         |
| 4,732,797 | A |   | 3/1988  | Johnson et al.    |         |
| 4,737,405 | A |   | 4/1988  | Bouchette         |         |
| 4,741,944 | A |   | 5/1988  | Jackson et al.    |         |
| 4,766,151 | A | * | 8/1988  | Leclerc et al.    | 514/640 |
| 4,772,501 | A |   | 9/1988  | Johnson et al.    |         |
| 4,865,221 | A |   | 9/1989  | Jackson et al.    |         |
| 4,904,524 | A |   | 2/1990  | Yoh               |         |
| 5,085,854 | A |   | 2/1992  | Fukuda et al.     |         |
| 5,141,803 | A |   | 8/1992  | Pregozen          |         |
| 5,152,996 | A |   | 10/1992 | Corey et al.      |         |
| 5,362,418 | A |   | 11/1994 | Yamasaki et al.   |         |
| 5,488,034 | A | * | 1/1996  | McGregor et al.   | 514/21.2 |
| 5,512,199 | A |   | 4/1996  | Khan et al.       |         |
| 5,538,732 | A |   | 7/1996  | Smith et al.      |         |
| 5,539,021 | A |   | 7/1996  | Pate et al.       |         |
| 5,688,842 | A |   | 11/1997 | Pate, III et al.  |         |
| 5,928,631 | A |   | 7/1999  | Lucas et al.      |         |
| 5,976,604 | A |   | 11/1999 | Kunieda et al.    |         |
| 6,159,487 | A | * | 12/2000 | Znaiden et al.    | 424/402 |
| 7,214,391 | B2 | * | 5/2007 | McDonald et al.   | 424/729 |
| 2001/0055609 | A1 |   | 12/2001 | Shantz et al.  |         |
| 2002/0035046 | A1 |   | 3/2002  | Lukenbach et al. |         |
| 2002/0123448 | A1 |   | 9/2002  | Dunn          |         |
| 2002/0128615 | A1 |   | 9/2002  | Tyrrell et al. |         |
| 2003/0027738 | A1 |   | 2/2003  | Delambre et al. |         |
| 2003/0049290 | A1 |   | 3/2003  | Jha et al.    |         |
| 2004/0121680 | A1 |   | 6/2004  | Yahiaoui et al. |         |
| 2004/0131660 | A1 | * | 7/2004 | Lange et al.  | 424/443 |
| 2005/0002974 | A1 |   | 1/2005  | Filbry et al. |         |

FOREIGN PATENT DOCUMENTS

| EP | 0328355 A     | 8/1989  |
| EP | 0615741 A     | 9/1994  |
| EP | 0759291 A     | 2/1997  |
| EP | 0 875 233 A1  | 11/1998 |
| EP | 0 808 151 B1  | 8/2001  |
| WO | WO 95/16824 A1 | 6/1995 |
| WO | WO 97/32559 A1 | 9/1997 |
| WO | WO 99/55303 A  | 11/1999 |
| WO | WO 02/00817 A1 | 1/2002 |
| WO | WO 02/41869 A2 | 5/2002 |
| WO | WO 02/076423 A2 | 10/2002 |

OTHER PUBLICATIONS

Abil Care 85 Technical Information, May 2003, Goldschmidt GmbH.*
CremoPhor CO Grades CremoPhor RH 40 Technical Information, Nov. 2002, BASF.*
The Merck Index, 1976, Merck % Co., Inc., (9$^{th}$ ed. By Martha Windholz), p. 1017, No. 7644.*
Lin T.J. et al. "Low-Energy Emulsification. Part VI: Applications in High-Internal Phase Emulsions", Jorunal of the Society Cosmetic Chemists, NewYork, NY, US, vol. 34, No. 7, Nov. 1984, pp. 357-368, X008022694 Introduction part on p. 357-358 figure 1; table 1.

* cited by examiner

*Primary Examiner* — Gina C Justice
(74) *Attorney, Agent, or Firm* — William E. Gallagher; Richard L. Alexander; Laura L. Whitmer

(57) ABSTRACT

The present invention describes an oil-in-water emulsion composition for wet-wipes delivering an improved body cleansing performance while providing a gentle and smooth feeling to the user.

19 Claims, No Drawings

COMPOSITION FOR WET WIPES THAT ENHANCES THE EFFICACY OF CLEANSING WHILE BEING GENTLE TO THE SKIN

CROSS REFERENCE TO RELATED APPLICATIONS

This application claims the benefit of U.S. Ser. No. 60/520,031, filed Nov. 14, 2003, and U.S. Ser. No. 60/485,848, filed Jul. 9, 2003.

FIELD OF INVENTION

This invention relates to a composition for a cleansing body wipe delivering an improved body cleansing performance while providing a gentle and smooth feeling to the user. The invention relates to the use of a composition comprising an emollient, a surfactant and/or emulsifier, a rheology modifier and preservative compounds, selected to deliver the intended benefits.

The present invention relates to personal care compositions, more particularly personal cleansing and/or skin treating compositions also providing a soothing benefit. The composition of the present invention is useful, for example, for gentle perineal and/or peri-anal cleansing and for protection against perineal dermatitis.

BACKGROUND OF THE INVENTION

Cleansing the skin is a personal hygiene problem not always easily solved. Dry tissue products are the most commonly used cleansing products post-defecation or post-urine release. Dry tissue products are usually referred to as "toilet tissue" or "toilet paper". Beside the use of dry tissue, it is becoming increasingly frequent to use wet wipes for the purpose of cleaning the anus, the perinea, and the peri-anal body area after defecation. So called "wet wipes" are a fibrous structure, generally of thick caliper, impregnated with a composition, usually water or oil-based.

For the purpose of the present document, the anus, the peri-anal area, the perinea and the perineal area are all terms indicating the body area of the pelvis between, around and including the anus and the external genitalia. Those terms are used interchangeably and with the same meaning.

The peri-anal skin is marked by the presence of fine folds and wrinkles (sulci) and by hair follicles, both of which make the perineal region one of the more difficult anatomical areas to cleanse. During defecation, fecal matter is excreted through the anus and tends to accumulate in hard to reach locations such as around the base of hairs and in the sulci of the skin's surface.

As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult. It is generally common hygienic concerns that make the benefits of a good perineal cleansing after defecation and after urine release very relevant to baby, children and adults.

Among those negatives associated with the failure of adequate cleansing are irritation, redness, desquamation, infections, unpleasant odor or other kinds of personal discomfort or health related issues.

People suffering from pathological conditions (such as hemorrhoids, fissures, cryptitis, etc.) are even more susceptible to those issues and discomfort. For them, as for any persons, cleansing must be efficient in terms of removal of fecal residues and gentle in terms of absence of irritation caused by the cleansing. Wet-wipes bring a response to that basic need.

In comparison to dry toilet paper, wet wipes have several benefits:
  The enabling of a better lubrication during the use of the wipe, reducing the abrasiveness of the cleansing operation,
  The hydration of the residues, enhancing their removal from the skin,
  The hydration of the skin tissue
  The ability to deliver a smoothening lotion to the skin that can remain on the skin after the cleansing operation.

Manufacturers and developers of wet wipes have tried to develop wipes products that deliver the right balance between normally antagonistic concepts:
  Enhancing the soil removal and protecting the skin from irritation.
  The long lasting feeling of comfortable cleanliness while avoiding a greasy feeling on the skin.
  High softness/smoothness of the substrate and its high resistance to disruption in use.
  The preservation of the product via the use of preservatives acting against microorganisms and a mild, skin friendly composition not causing irritation or redness.

For example, the Pampers Baby Fresh & reg. baby wipes are marketed with a patent marking of U.S. Pat. No. 4,904,524.

The use of emulsions in lotion for wipes is widely spread. Most commonly used emulsions are an oil-in-water type of emulsion, having as key components an oily phase (in the form of an emollient), an emulsifier or surfactant component and an aqueous phase that comprises further additives such as antimicrobial agents.

Many patent documents intend to describe wipes with lotion:

In EP808151B1, Blieszner et al, describe a composition for wipes and wipes using a composition that is useful for personal cleansing and for reducing the risk of perineal dermatitis. In WO-9516824 Warner et al. describe a lotion composition that is semisolid or solid at ambient temperatures and imparts a soft, lubricious, lotion-like feel when applied to tissue paper. This lotion comprises about 20 to about 95% of a substantially water free emollient having a plastic or fluid and from about 5 to about 80% of an agent capable of immobilizing the emollient on the surface of tissue.

In WO-0241869, Hsu, Jay, C. et al. describe a paper product treated with oil-in-water emulsions. The paper product contains a lotion, an emollient, a fatty alcohol component, an emulsifier component, and a skin conditioning component. All components presenting a defined percentage of the lotion and paper product.

In EP-875233 A1, Luu, Phunong, V. et al. describe a substrate treated with a lotion comprising emollient and a retention/release agent. A substrate treated with the non-greasy-feeling lotion provides a smooth, lubricious, non-greasy-feeling layer on the skin.

In WO-0200817, C. Druden, describes a wipe using cocamidopropyl betaine and PEG-80 glyceryl cocoate/PEG-30 glyceryl cocoate for an improved cleansing ability.

U.S. Pat. Nos. 4,741,944 and 4,865,221 provide wet wipes having a liquid in the sheet and/or web. The liquid includes water, benzalkonium chloride, citric acid, disodium phosphate, trisodium ethylene diamine tetraacetic acid, polyethylene glycol-75 lanolin, cocoamphocarboxyglycinate, propylene glycol, methylparaben, propylparaben, butylparaben, polysorbate 20 and fragrance.

U.S. Pat. Nos. 4,732,797 and 4,772,501 are directed to a natural acid preservation system for a wet wipe that consists of citric acid and sorbic acid. U.S. Pat. No. 5,141,803 provides a nonwoven wipe impregnating composition. A specific cationic biocide is included in the preservative system. The cationic biocide, polyhexamethylene biguanide hydrochloride, allegedly greatly minimizes the slippery feel of the wet wipe.

U.S. Pat. No. 4,737,405 is directed to a binder catalyst for an antimicrobial active, non-woven web. U.S. Pat. No. 5,512,199 is directed to a hand wipe that includes an alcohol, an antimicrobial agent, a water soluble polymer, a polyalkylene glycol and a moisturizer and/or emollient, along with water.

Also, U.S. Pat. No. 5,152,996 is directed to a non-woven wipe impregnated with an aqueous solution of a zinc acetate peroxide and a surfactant.

General background on emulsions and their potential use (e.g., in cosmetics) can be found in:
- U.S. Pat. No. 4,606,913 describing high internal phase emulsions having enhanced stability and their use in cosmetics.
- U.S. Pat. No. 5,539,021 and U.S. Pat. No. 5,688,842 describing a method for making a high internal phase emulsion without phase inversion.
- U.S. Pat. No. 5,362,418 describing an oil-in-water gel-like emulsion comprising mono-alkyl phosphate salt.
- U.S. Pat. No. 5,085,854 describing a translucent cosmetic emulsion comprising mono-alkyl phosphate salt.
- U.S. Pat. No. 5,976,604 and U.S. Pat. No. 4,379,755 describing an oil-in-water emulsion with high oil content, comprising a sucrose fatty ester.
- WO 97/32559 describing a stable dispersion having a bi-liquid foam comprising oil droplets and suitable for cosmetic applications.

Many of the above documents are directed at finding alternatives or improved ways to deliver better wipes performance. However, many of the drawbacks and inconveniences experienced by the consumers still represent clear challenges to product developers in the field. For example, preservatives sometimes cause sting, redness and irritation of the skin, lotions feel greasy and leave stains, separation of the phases (oil/water) occurs during storage, lotions enhance the spread of the fecal residue on the skin without facilitating their removal and pick up by the wipe.

Altogether, the need to achieve an improved level of smoothness and gentle cleanliness during and after cleaning and wiping still remain a basic need articulated by many consumers. There is the need for an emulsion composition providing sufficient preservation combined with superior gentleness to the skin. There is also the need for a wipe that enhances the efficacy of the removal of the fecal residues from the peri-anal/perineal area. Additionally, there is a need for a wipe that does not irritate, erode the user's skin nor enhance redness.

Furthermore, there is the need for a wipe providing a smooth, long lasting comfortable feeling to the user, without leaving greasy or oily residues on the skin. There is also the need for a wipe that has a long shelf life and whose composition reduces the proliferation of microorganisms in the package and during use. Additionally, there is the need for an emulsion composition that is relatively easy and cost efficient to prepare and preserve. There is finally the need for a wipe combining all or most of the above benefits to a so far unachieved level.

SUMMARY OF THE INVENTION

The present invention describes a composition that can be used for a body-cleaning wipe intended to clean areas such as the perineal area after defecation or the release of urine. The present invention addresses the problem of delivering a highly efficient cleansing together with best skin gentleness and best comfort.

In one embodiment, the composition includes an emollient having a low surface tension, representing from about 0.001% to less than about 5% of the composition, a surfactant and/or emulsifier having a low surface tension, preservative compounds exhibiting a high rate of killing as well as a high gentleness to skin and optionally a rheology modifier.

In another embodiment of the present invention, the composition comprises an emollient, a surfactant and a rheology modifier that create an overall composition of medium to low surface tension. It also comprises a paraben antimicrobial.

In another aspect, the invention comprises a wet-wipe comprising such composition exemplified above.

The concept around the present invention resides in the careful selection of the above compounds and chemicals to deliver the intended results. The present invention defines the characteristics of the compounds and chemicals suitable for the present invention. It has been demonstrated by the inventors that the compounds and chemicals selected can surprisingly work synergistically, if selected and combined as per the present invention. In particular, the selection of particular surfactants, emollients and soothing agents allows for the concomitant use of very effective preservatives that otherwise would cause stinging, redness and irritation.

All documents cited are, in relevant part, incorporated herein by reference; the citation of any document is not to be construed as an admission that it is prior art with respect to the present invention.

DETAILED DESCRIPTION OF THE INVENTION

Wet-Wipes

The present invention proposes a composition for wet-wipes. Wet wipes or wipes or wet-tissues are the general terms to describe a piece of material, generally non-woven material, used to cleanse body parts. In particular, most currently available wipes are intended for the cleaning of the peri-anal area after defecation. Other wipes are available for the cleansing of the face or other body parts. The present invention focuses on wipes for the peri-anal (or perineal) area but is not limited to this particular type of wet wipes. Wet-wipes are generally of sufficient dimension to allow for convenient handling while being small enough to be easily disposed of by the sewage system or discretely disposed of in garbage bins. The material of the wipes is generally soft and flexible, potentially having a structured surface enhancing its cleaning performance. The material is preferably a non-woven material, generally made of synthetic compounds. However, woven materials as well as the use of natural compounds in either woven or nonwoven materials are within the scope of the present invention. The texture and material of the wipe are of high relevance to the performance of the wipe. In one embodiment of the present invention the non-woven material comprises fibers selected from the group consisting of polyolefin, polyester, cellulose, rayon, polyamides, polyesteramide, polyvinyl alcohols, and combinations thereof. The substrate usable for this invention can be manufactured via any suitable process, such as but not limited to, spunlace process and preferably has a dry basis weight of between about 45 grams per square meter (gsm) and 75 gsm, more preferably between 45 gsm and 65 gsm.

Wipes are generally impregnated with a liquid or semi liquid composition, intended to both enhance the cleaning and to provide a smooth feeling. Generally the composition is of sufficiently low viscosity to impregnate the entire structure of the wipe. In some other instances, the composition can be primarily present at the wipe surface and to a lesser extent in the inner structure of the wipe. In one optional embodiment the composition is releasably carried by the material, that is, the composition is contained either in or on a substrate and is readily releasable from the substrate by applying some force to the substrate, for example, wringing the substrate, or wiping a surface, such as a child's bottom, with the wet-wipe.

Soothing/Cleansing Composition:

The composition impregnating the wipe is commonly and interchangeably called lotion, smoothening lotion, smoothening composition, oil-in-water emulsion composition, emulsion composition, emulsion, cleaning or cleansing lotion or composition. All those terms are hereby used interchangeably and indicate the dual basic function of the composition of the present invention: enhanced cleansing and delivery of a skin smoothening effect.

In one optional embodiment, the composition of the present invention comprises, but is not limited to:
An emollient
A surfactant and/or an emulsifier
A soothing agent
Optionally a rheology modifier
A preservative, or more specifically a multiplicity of preservative compounds acting together as a preservative system.
water It is to be noted that some compounds can have a multiple function and that all compounds are not necessarily present in the composition of the invention.

The composition of the present invention is a so called oil-in-water emulsion: Small oil droplets are dispersed and surrounded by a hydrophilic medium.

Preferably the composition of the present invention has a surface tension of less than about 35 mN/m, more preferably less than about 30 mN/m, and even more preferably less than about 25 mN/m.

The pH of the composition is from about pH 3 to about pH 9, preferably from about pH 4 to about pH 7.5, more preferably from about pH 5 to about pH 7.

Emollient:

Common dictionaries define "emollient" as "something that softens or soothes". Their functions in a wet-wipe include (1) to improve the glide of the wipe on the skin, by enhancing the lubrication and thus decreasing the abrasion of the skin, (2) to hydrate the residues (for example fecal residues or dried urine residues), thus enhancing their removal from the skin, (3) to hydrate the skin, thus reducing its dryness and irritation while improving its flexibility under the wiping movement, (4) to protect the skin from later irritation (for example caused by the friction of underwear) as the emollient is deposited onto the skin and remains at its surface as a thin protective layer.

In one embodiment of the present invention, preferred emollients are silicon based. Silicone-based emollients are organo-silicone based polymers with repeating siloxane (Si—O) units. Silicone-based emollients of the present invention are hydrophobic and exist in a wide range of possible molecular weights. They include linear, cyclic and cross-linked varieties. Silicone oils are generally chemically inert and usually have a high flash point. Due to their low surface tension, silicone oils are easily spreadable and have high surface activity. Examples of silicon oil for the present invention include: Cyclomethicones, Dimethicones, Phenyl-modified silicones, Alkyl-modified silicones, Silicones resins, Silica.

Other emollients useful in the present invention can be unsaturated esters or fatty esters. Examples of unsaturated esters or fatty esters of the present invention include: Caprylic Capric Triglycerides in combination with Bis-PEG/PPG-16/16 PEG/PPG-16/16 Dimethicone and $C_{12}$-$C_{15}$ Alkylbenzoate.

The amount of emollient that can be included in the lotion composition will depend on a variety of factors, including the particular emollient involved, the lotion-like benefits desired, and the other components in the lotion composition. It has been found that compositions with low or very low emollient content are best suited for the invention: The emollient content of the composition is from about 0.001% to less than about 5%, preferably from about 0.001% to less than about 3%, more preferably from about 0.001% to less than about 2.5% and even more preferably from about 0.001% to less than about 1.5% (all % are weight/weight % of the emollient in the composition). Without being bound by the theory, it is believed that a low emollient content decreases the risk of oil/greasy deposit onto the skin (that the users would rate negatively as to the comfort and likeability).

It has surprisingly been found by the inventors that emollients presenting a relatively low surface tension act more efficiently in the composition proposed by the present invention. Surface tension lower than about 30 mN/m is preferable, most preferably lower than about 20 mN/m.

Preferably, the emollient of the present invention has a medium to low polarity. Also, preferably the emollient of the present invention has a solubility parameter between about 5 and about 12, most preferably between about 5 and about 9.

The basic reference of the evaluation of surface tension, polarity, viscosity and spreadability of emollient can be found under Dietz, T., Basic properties of cosmetic oils and their relevance to emulsion preparations. SÖFW-Journal, July 1999, pages 1-7.

Emollients particularly suited for the present invention are selected from a list comprising Dimethiconol, Dimethicone, Cyclopentasiloxane, Caprylic/Capric Triglyceride, $C_{12}$-$C_{15}$ Alykylbenzoate or a mixture of Caprylic Capric Triglyceride and Bis-PEG/PPG-16/16 PEG/PPG-16/16 Dimethicone, and any combination thereof.

Emulsifier/Surfactant:

The composition also includes an emulsifier such as those forming oil-in-water emulsions. The emulsifier can be a mixture of chemical compounds and include surfactants. The preferred emulsifiers are those acting as well as a surfactant. For the purpose of this document, the terms emulsifiers and surfactants are thereafter used interchangeably. The emulsifier may be a polymeric emulsifier or a non polymeric one.

The emulsifier is employed in an amount effective to emulsify the emollient and other non-water-soluble oils that may be present in the composition, preferably an amount ranging from about 4% to about 0.001%, more preferably from about 1% to about 0.01%, even more preferably about 0.5% to about 0.02% (based on the weight emulsifiers over the weight of the composition). Mixtures of emulsifiers may be used.

Surfactants/emulsifiers having a low viscosity are preferred for the present invention. Low viscosity is understood to mean viscosity of less than about 15,000 cps at about 25 degrees Celsius of a 1% aqueous solution of the surfactant as measured by a Brookfield apparatus as described in the method part of this document. More preferably the viscosity is less than about 10,000 cps under the same conditions.

Other characteristics of preferable surfactants/emulsifiers include high polarity and a non-ionic nature.

Particularly suited for the present invention are emulsifiers such as Alkylpolylglucosides, Decylpolyglucoside, fatty alcohol or alkoxylated fatty alcohol phosphate esters (e.g., Trilaureth-4 Phosphate), Sodium Trideceth-3 Carboxylate, or a mixture of Caprylic Capric Triglyceride and Bis-PEG/PPG-16/16 PEG/PPG-16/16 Dimethicone, Polysorbate 20, and combinations thereof.

Without being bound by the theory, it is believed that a non-ionic surfactant/emulsifier having a low viscosity is best to enable the emulsification of an emollient of low surface tension. The combination delivers a relatively stable emulsion of low oil droplet size.

Rheology Modifier

It has been found that the rheology of the composition plays a significant role in its functionality. A series of compounds aimed at insuring the desired rheology have been found to be preferable. These compounds are also called stabilizers for their role in the stabilization of the composition.

Rheology modifiers are compounds that increase the viscosity of the composition at lower temperatures as well as at process temperatures. Rheology modifiers or suspending agents or stabilizers also provide "structure" to the compositions to prevent settling out (separation) of insoluble and partially soluble components. Other components or additives of the compositions may affect the temperature viscosity/rheology of the compositions.

The effect and advantage of rheology modifiers are in particular described in US20020128621A1 entitled "Absorbent articles with simplified compositions having good stability" published on Sep. 12, 2002, filed on Dec. 21, 2001, by Kruchoski et al., and US20020128615A1 entitled "Absorbent articles with non-aqueous compositions containing anionic polymers" published on Sep. 12, 2002, filed on Dec. 22, 2001, by Tyrrell et al.

In addition to stabilizing the suspension of insoluble and partially soluble components, the rheology modifiers of the invention also help to stabilize the composition on the wipe and enhance the transfer of lotion to the skin: The wiping movement increases the shear and pressure therefore decreasing the viscosity of the lotion and enabling a better transfer to the skin as well as a better lubrication effect.

Additionally, the rheology modifier helps to preserve a homogeneous distribution of the composition within the wipe stack: Any fluid composition has a tendency to migrate to the lower part of the wipes stack during prolonged storage. This effect creates an upper zone of the stack having less composition than the bottom part. This is seen as a sign of relatively low quality by the users.

Preferred rheology modifiers exhibit low initial viscosity and high yield. Particularly suited for the present invention are rheology modifiers such as, but not limited to:

Blends of material as are available from Uniqema GmbH&Co. KG, of Emmerich, Germany under the trade name ARLATONE. Particularly preferred are ARLATONE V-175 which is a blend of sucrose palmitate, glyceryl stearate, glyceryl stearate citrate, sucrose, mannan, and xanthan gum, and ARLATONE V-100 which is a blend of Steareth-100, Steareth-2, glyceryl stearate citrate, sucrose, mannan, and xanthan gum.

Blends of material as are available from Seppic France of Paris, France as SIMULGEL. Particularly preferred is SIMULGEL NS which comprises blends of hydroxyethylacrylate/sodium acryloyldimethyl taurate copolymer and squalene and polysorbate 60, Sodium acrylate/Sodium acryloyldimethyltaurate copolymer and polyisobutene and capryryl capryl glucoside, Acrylate copolymers, such as but not limited to acrylates/acrylamide copolymer, mineral oil, and Polysorbate 85.

Acrylate homopolymers, Acrylate crosspolymers, such as but not limited to Acrylate/C10-30 Alkyl Acrylate crosspolymers, carbomers, such as but not limited to acrylic acid cross linked with one or more allyl ether, such as but not limited to allyl ethers of pentaerythritol, allyl ethers of sucrose, allyl ethers of propylene, and combinations thereof as are available as the Carbopol® 900 series from Noveon, Inc. of Cleveland, Ohio (e.g., Carbopol® 954).

Naturally occurring polymers such as xanthan gum, Galactoarabinan and other polysaccharides.

Combinations of the above rheology modifiers.

Examples, of commercially available rheology modifiers include but are not limited to, Ultrez-10, a carbomer, and Pemulen TR-2, an Acrylate crosspolymers, both of which are available from Noveon, Cleveland Ohio, USA, and Keltrol, a xanthan gum, available from CP Kelco San Diego Calif., USA.

Rheology modifiers, when present may be used in the present invention at a weight/weight % (w/w) from about 0.01% to about 3%, preferably from about 0.015% to about 2%, more preferably from about 0.02% to about 1%.

Preservative:

The need to control microbiological growth in personal care products is known to be particularly acute in water based products such as non-ionic oil-in-water emulsions and in pre-impregnated wipes such as baby wipes.

The composition of the present invention comprises a preservative compound or more preferably a combination of preservative compounds acting together as a preservative system. Preservative and preservative systems are used interchangeably in the present document to indicate one unique or a multiplicity of preservative compounds.

A preservative is understood to be a chemical or natural compound or a multiplicity of compounds reducing the growth of microorganisms, thus enabling a longer shelf life for the pack of wipes (opened or not opened) as well as creating an environment with reduced growth of microorganisms when transferred to the skin during the wiping process.

Preservatives of the present invention can be defined by 3 key characteristics: (1) An activity against a large spectrum of microorganisms, that may include bacteria and/or molds and/or yeast, preferably all three categories of microorganisms together; (2) The killing efficacy and/or the efficacy to reduce the growth rate at a concentration as low as possible; and (3) The gentleness to the skin.

The spectrum of activity of the preservative of the present invention may include bacteria, molds and yeast. More preferably the preservative is active against bacteria and molds and yeast.

The preferred preservative according to the present invention actively kills the microorganisms. Another mode of action to be contemplated is the reduction of the growth rate of the microorganisms without active killing. Both actions however result in a drastic reduction of the population of microorganisms.

It is easily understood that concentration of preservative is desirably as low as possible while achieving the targeted efficacy. With regard to its acceptability there are, in many countries, laws and regulations governing the maximum permitted content of preservative in products intended for human use due to their possible toxic or otherwise harmful effect. Still being within the permitted limits some preservatives can induce inconvenience for the consumers (such as mild irritation, redness, sting, etc.). Net, at least three driving forces command levels of preservatives as low as possible: the legal regulations, the possible skin effect to the consumers and the cost of the raw material. It is an objective of the present invention to provide an efficient technical solution to ensure a low concentration of preservative while preserving its efficacy.

The gentleness to skin is a key characteristic of the preservative of the present invention. It is to be understood that the preservative comes in contact with the skin during the wiping operation. As some lotion remains on the skin after use, the time of contact between the preservative and the skin can be extended (for example, several hours). Therefore the preservative needs to be in a form that is well tolerated by the skin, without causing skin redness, desquamation, allergic reaction, irritation, burning feeling, sting or other types of inconvenience.

Gentleness to skin can be measured as "gentleness index" versus water (water being considered most gentle to skin). The method is described in this document.

It has been found that a gentleness index of below about 0.3, preferably less than about 0.2, more preferably less than about 0.15, provides a much reduced irritation of the skin.

The preservative of the present invention (or preservative system) comprises at least one paraben antimicrobial. Preferably the preservative is a paraben antimicrobial selected from the list of: Methylparaben, Ethylparaben, Propylparaben, Butylparaben, Isobutylparaben or combinations thereof.

The total concentration of paraben antimicrobial encompassed by the present invention is preferably lower than about 1%, more preferably lower than about 0.5%, even more preferably lower than about 0.3%. (It is to be noted that legal requirements may restrict those ranges in practice.) The minimum amount of paraben antimicrobial is any amount sufficient to obtain the desired preservation of the composition, in most embodiments of the invention more than 0.001% (w/w).

Such a preservative system can show a synergistic preservative action greater than would be expected from the single components acting independently. This synergistic action can produce a broad anti-microbial effect and can permit use of the preservative system at a low level concentration.

The present chemical composition can moreover provide a broad anti-microbial effect without the use of formaldehyde donor derived products. These traditional formaldehyde based preservatives have been widely used in the past but are now no longer permitted in a number of countries for products intended for human use.

The present preservative system can conveniently be supplied to a manufacturer as a ready dissolved solution. Even more conveniently, the preservative system can be supplied in pre-measured dosed quantities.

The preservative(s) of the present invention may be complemented by a variety of other preservatives of same or other classes, to form a preservation system.

Soothing Agent:

Soothing agents are compounds having the ability to reduce the irritation or stinging/burning/itching effect of some chemicals. Soothing agents can be of a variety of chemical classes. Soothing agents can have a variety of mode of actions to neutralize the effects of the skin irritants especially for paraben based preservative systems. For example antioxidants can be soothing agents for oxidants. Buffers can be soothing agents neutralizing the stinging effect on skin of acids or bases. It is to be noted that emollients can also be soothing agents. Soothing agents that act against the stinging/irritation effect of some preservatives are preferred. Those soothing agents can be emollients or surfactants helping, for example, the solubilization or the micellization of the preservatives.

The preferred soothing agents of the present invention are (a) ethoxylated surface active compounds, more preferably those having an ethoxylation number below about 60, (b) polymers, more preferably Polyvinylpirrolidone (PVP) and/or N-Vinylcaprolactam Homopolymer (PVC), and (c) Phospholipids, more preferably phospholipids complexed with other functional ingredients as e.g., fatty acids, organosilicones.

Most preferably the soothing agents of the present invention are selected from the below compounds and combinations thereof: PEG40 Hydrogenated Castor Oil, Sorbitan Isostearate, Isoceteth-20, Sorbeth-30, Sorbitan Monooleate, Coceth-7, PPG-1-PEG-9 Lauryl Glycol Ether, PEG-45 Palm Kernel Glycerides, PEG-20 Almond Glycerides, PEG-7 Hydrogenated Castor Oil, PEG-50 Hydrogenated Castor Oil, PEG-30 Castor Oil, PEG-24 Hydrogenated Lanolin, PEG-20 Hydrogenated Lanolin, PEG-6 Caprylic/Capric Glycerides, PPG-1 PEG-9 Lauryl Glycol Ether, Lauryl Glucoside Polyglyceryl-2 Dipolyhydroxystearate, Sodium Glutamate, Polyvinylpyrrolidone, N-Vinylcaprolactam Homopolymer, Sodium Coco PG-Dimonium Chloride Phosphate, Linoleamidopropyl PG-Dimonium Chloride Phosphate, Sodium Borageamidopropyl PG-Dimonium Chloride Phosphate, N Linoleamidopropyl PG-Dimonium Chloride Phosphate Dimethicone, Cocamidopropyl PG-Dimonium Chloride Phosphate, Stearamidopropyl PG-Dimonium Chloride Phosphate and Stearamidopropyl PG-Dimonium Chloride Phosphate (and) Cetyl Alcohol Optional Components of the Composition:

The composition of the claimed invention may optionally include adjunct ingredients. Possible adjunct ingredients may be selected from a wide range of additional ingredients such as, but not limited to perfumes and fragrances, texturizers, colorants, medically active ingredients, in particular healing actives and skin protectants.

Preparation of the Composition:

The composition of the present invention and wipes comprises the compositions, can be made by the conventional processes described in the art and references therein. Alternatively, the composition and wipes are made according to copending U.S. Provisional Patent Application No. 60/520,032 entitled "A PROCESS FOR MAKING A WET WIPE USING A CONCENTRATED EMULSION" by Sylvie Chamba et al., Procter & Gamble and filed on Nov. 14, 2003.

Article of Commerce:

In one embodiment of the present invention an article of commerce is provided. The article of commerce of the present invention typically comprises (a) a container as described herein, and (b) at least wet wipe as described herein.

Containers useful in the present article include but are not limited, for example, PET tubs, flow wrap pouches, precut sachets for individually packed cleansing mitt, and other packaging known in the art as suitable for nonwoven article. Additionally, the container can also be manufactured to facilitate removal of individual cleansing wet wipes.

The container can be made of any suitable material or materials, and can be manufactured in any suitable manner. For example, the container can be made of polystyrene, polypropylene, PET, POET, polyethylene, polyester, polyvinyl alcohol, or the like. The containers may also be made of mixtures of materials. The containers can be manufactured by, for example, a vacuum molding process or an injection molding process, or any suitable process.

Additional information on containers, as well as additional option components for containers, including but not limited to: container bodies; lids; containers features, such as but not limited to, attachments of lids, hinges, zippers, securing means; and the like, can be found in U.S. Pat. Nos. Des 451,279; Des 437,686; Des 443,508; Des 443,451; Des 421,901; Des 421,902; Des 416,794; Des 414,637; Des 445,329; 3,982,659; 3,967,756; 3,986,479; 3,994,417; 6,269,970; 5,785,179; 5,366,104; 5,322,178; 5,050,737; 4,971,220; 6,296,144; 6,315,114; 4,840,270; 4,471,881; 5,647,506; 6,401,968; 6,269,969; 6,412,634; 5,791,465; 6,092,690; and 6,092,690; U.S. Patent Application Publication No. 2002/0064323 published on May 30, 2002, inventor Chin; and WO 00/27268 published on May 18, 2000, and assigned to The Procter & Gamble Co.; WO 02/14172 published on Feb. 21, 2002, and assigned to The Procter & Gamble Co.; and WO 99/55213 published on Nov. 4, 1999, and assigned to The Procter & Gamble Co.

Synergistic Effect of the Composition:

It has been found that the compositions of the present invention can deliver both a reduced skin gentleness index and a satisfactory cleaning of the skin. It has been found that only a composition exhibiting the claimed skin gentleness index below about 0.3 is able to deliver strong benefits to the users, i.e. a low irritation together with an enhanced cleansing ability and a microbiologically stable composition.

It has been found that compositions with a skin gentleness index above about 0.3 would induce some level of sting when applied by the users.

It has been found that a composition comprising less than about 5% emollient and a paraben based preservative would generally not deliver skin gentleness index of less than about 0.3. It has been found that only the combination of the described preservative system, soothing agent, and surfactant of low viscosity can deliver the claimed gentleness benefits.

It has also been found that some or all of the indicated benefits of the present invention can be achieved by use of the preferred compounds as described, in a way which delivers a skin gentleness index below about 0.3 as defined in the primary claim.

Table 1 shows examples of formulations. Formulation Ref. 1 exhibits a skin gentleness index of about 1.53 while using no soothing agent. Formulation Ref. 2 exhibits a skin gentleness index above 0.3 when using a soothing agent at a low about 0.4% level. In contrary, Inv 1, Inv 2 and Inv 3 are examples of the present invention and thus exhibit a skin gentleness index below about 0.3. The examples of the present invention also comprise a surfactant according to the teaching of the invention.

TABLE 1

| Formulation # | Matrix | Paraben Levels | Soothing Agent % (w/w) | Emollient % (w/w) | Skin gentleness index |
|---|---|---|---|---|---|
| Ref 1 | 14-A | 0.15% Methylparaben 0.05% Propylparaben 0.05% Ethylparaben | 0% | 0.45% | 1.53 |
| Ref 2 | 14-A | 0.15% Methylparaben 0.05% Propylparaben 0.05% Ethylparaben | 0.40% | 0.45% | 0.69 |
| Inv 1 | 14-A | 0.15% Methylparaben 0.05% Propylparaben 0.05% Ethylparaben | 1.20% | 0.45% | −0.06 |
| Inv 2 | 14-A | 0.15% Methylparaben 0.05% Propylparaben 0.05% Ethylparaben | 0.80% | 0.45% | 0.00 |
| Inv 3 | 17-A | 0.15% Methylparaben 0.05% Propylparaben 0.05% Ethylparaben | 0.80% | 1.50% | −0.06 |

EXAMPLES

Examples A, B, C and D are examples of the present invention, thus exhibiting a skin gentleness index below 0.3. Their composition is detailed respectively in tables A, B, C and D.

Example A

TABLE A

| Component | Amount (% by weight) |
|---|---|
| (1) Disodium EDTA | 0.10 |
| (2) Arlatone-V 175 ™* | 0.80 |
| (3) Decylglycoside | 0.05 |
| (4) Cyclopentasiloxane Dimethiconol | 0.45 |
| (5) 1,2-Propyleneglycol | 1.50 |
| (6) Phenoxyethanol | 0.80 |
| (7) Methylparaben | 0.15 |
| (8) Propylparaben | 0.05 |
| (9) Ethylparaben | 0.05 |
| (10) PEG-40 Hydrogenated Castor Oil | 0.80 |
| (11) Perfume | 0.05 |
| (12) Purified water | Balance |
| Total | 100.00 |

*Arlatone-V 175 ™ comprises sucrose palmitate, glyceryl stearate, glyceryl stearate citrate, sucrose, mannan, xanthan gum and is commercialized by Uniqema GmbH & Co. KG, 46429 Emmerich, Germany, www.uniqema.com.

Example B

TABLE B

| Component | Amount (% by weight) |
|---|---|
| (1) Disodium EDTA | 0.10 |
| (2) Arlatone-V 175 ™* | 0.80 |
| (3) Abil Care 85 ™** | 0.45 |
| (4) Decylglycoside | 0.05 |
| (5) 1,2-Propyleneglycol | 1.50 |
| (6) Sodium benzoate | 0.20 |
| (7) Methylparaben | 0.15 |
| (8) Propylparaben | 0.05 |
| (9) Ethylparaben | 0.05 |

TABLE B-continued

| Component | Amount (% by weight) |
|---|---|
| (10) PEG-40 Hydrogenated Castor Oil | 0.80 |
| (11) Perfume | 0.05 |
| (12) Purified water | Balance |
| Total | 100.00 |

*Arlatone-V 175 ™ comprises sucrose palmitate, glyceryl stearate, glyceryl stearate citrate, sucrose, mannan, xanthan gum and is commercialized by Uniqema GmbH & Co. KG, 46429 Emmerich, Germany, www.uniqema.com.
**Abil Care 85 ™ comprises Bis-PEG/PPG-16/16 PEG/PPG Dimethicone Caprylic Capric triglyceride and is commercialized by Goldschmidt/Degussa, Goldschmidt AG, 45127 Essen, Germany www.goldschmidt.com.

Example C

TABLE C

| Component | Amount (% by weight) |
|---|---|
| (1) Disodium EDTA | 0.10 |
| (2) Arlatone-V 175 ™* | 0.80 |
| (3) Cyclopentasiloxane Dimethiconol | 0.36 |
| (4) Glycerin | 0.067 |
| (5) Sodium trideceth carboxylate | 0.022 |
| (6) 1,-Propyleneglycol | 1.50 |
| (7) Phenoxyethanol | 0.60 |
| (8) Methylparaben | 0.15 |
| (9) Propylparaben | 0.05 |
| (10) Ethylparaben | 0.05 |
| (11) PEG-40 Hydrogenated Castor Oil | 0.80 |
| (12) Perfume | 0.05 |
| (13) Purified water | Balance |
| Total | 100.00 |

*Arlatone-V 175 ™ comprises sucrose palmitate, glyceryl stearate, glyceryl stearate citrate, sucrose, mannan, xanthan gum and is commercialized by Uniqema GmbH & Co. KG, 46429 Emmerich, Germany, www.uniqema.com.

Example D

TABLE D

| Component | Amount (% by weight) |
|---|---|
| (1) Disodium EDTA | 0.10 |
| (2) Polysorbate 20 | 0.50 |
| (3) Simulgel NS ™* | 1.00 |
| (4) Abil Care 85 ™** | 1.00 |
| (5) Dimethicone | 1.00 |
| (6) C12-13 Alkylbenzoate | 050 |
| (7) 1,2-Propyleneglycol | 1.50 |
| (8) Sodium benzoate | 0.20 |
| (9) Methylparaben | 0.15 |
| (10) Propylparaben | 0.05 |
| (11) Ethylparaben | 0.05 |
| (12) PEG-40 Hydrogenated Castor Oil | 0.80 |
| (13) Perfume | 0.05 |
| (14) Purified water | Balance |
| Total | 100.00 |

*Simulgel NS ™ comprises Hydroxyethylacrylate/Sodium Acryloyldimethyltaurat copolymer & polysorbate60 and is commercialized by Seppic France, 75 Quai D'Orsay, 75321 Paris Cedex 07, France, www.seppic.com.
**Abil Care 85 ™ comprises Bis-PEG/PPG-16/16 PEG/PPG Dimethicone Caprylic Capric triglyceride and is commercialized by Goldschmidt/Degussa, Goldschmidt AG, 45127 Essen, Germany www.goldschmidt.com.

The skin gentleness index of the composition of example D is 0.09.

Example F

Wet-Wipe

Examples A-E show formulations of the present invention that can be combined with substrate comprising 60% (w/w) polypropylene fibers and 40% (w/w) viscose fibers and having a average fiber lengths being about 38 mm to 40 mm (available for example from PGI, USA), to prepare a wet-wipe in accordance with the present invention.

The water used in the examples of this invention as well as in its description, methods and teaching is water of cosmetic grade or pharmaceutical grade, preferably deionized water, interchangeably referred to as "purified water" or "water".

Methods

Measurement of Surface Tension:

The methodology used for measuring surface tension of fluid is the so-called Wilhelmy plate Method. The Wilhelmy plate method is a universal method especially suited to check surface tension over time intervals. In short, a vertical plate of known perimeter is attached to a balance, and the force due to wetting is measured.

The equipment used and corresponding settings are as follows:

Device: Krüss Tensiometer K12, manufactured by Krüss GmbH, Borsteler Chausee 85-99a, 22453 Hamburg—Germany, Phone: +49 40 51 44 01-0, www.kruess.com.

Plate Dimensions: Width: 19.9 mm Thickness: 0.2 mm, Height: 10 mm.

Measurement Settings: immersion depth 2 mm, Surface Detection Sensitivity 0.01 g, Surface Detection Speed 6 mm/min, Values 10, Acquisition linear, Max. Measurement Time 60 sec.

The liquid to be measured is poured into a clean and dry glass vessel. The sample temperature is controlled at 25° C. The clean and annealed Wilhelmy plate is lowered to the surface of the liquid. The plate is immersed in the fluid to measure and the corresponding value of surface tension is read on the display of the device. Instructions can be found in the user manual edited by "Krüss GmbH Hamburg 1996" Version 2.1.

Measurement of Viscosity:

Viscosity measurements are performed with a Brookfield apparatus RVDVIII digital rheometer (Brookfield Engineering Laboratories, INC., 11 Commerce Boulevard, Middleboro, Mass. 02346 U.S.A., www.brookfieldengineering.com). The liquid to be measured is poured into a clean and dry glass beaker. The sample temperature is controlled at 25° C. The used spindle geometry is a disc spindle (disc spindle RV, no 6), used speed is 20 rpm and the value is recorded 1 minute after the measurement was started. The method is described in the User Manual: M/98-211 edited by the manufacturer of the equipment.

Solubility Parameters:

Information, data and measurement methods regarding solubility parameters can be found in "Cosmetics and Toiletries", Vol 103, October 1988, page 47 to 64.

Skin Gentleness Index:

The skin gentleness index of a composition is measured via a blind study in a controlled environment among panelists under clinical testing conditions.

Panelist Recruiting:

Volunteers from a panel of screened sting sensitive subjects who show no evidence of active dermatological disease and no evidence of damaged skin on the nasolabial folds are enrolled in the study. Upon enrollment subjects are reminded not to use skin care and/or skin cleaning products in the face, starting the night before the visit and during the duration of the study.

Panelist screening is done with a 10% Lactic acid solution in water on subjects with uncompromised skin in the nasolabial fold vs. a water control on the respective other nasolabial fold (see below for application of solutions). Success criteria for enrollment are at least a 2 score for the Lactic acid and a difference of at least 1 score vs. water during the screening visit. At least 15 panelist per test are necessary. One test will allow to evaluate the skin gentleness index of one lotion composition versus water.

Application of Solutions:

In a controlled environment with RH of 30-50% and an air temperature of 20-23 degree C. fresh cotton tipped applicators (any type of commercial Q-tips are suitable) are dipped into the test solution and applied with 5 strokes using moderate pressure on the nasolabial fold. Each stroke will be with an outward motion starting at the nasolabial fold. Water is used as a reference fluid and is applied on one nasolabial fold while the test solution is applied on the respective other nasolabial fold. The nasolabial fold sides for the application of the water and test solution will be randomized across subjects, following a study specific randomization scheme. Panelists are required to have at least a rest period of 4 weeks before repeated selection for another test.

Skin Gentleness Evaluation:

Stinging/burning is evaluated 2 minutes after product application by asking the candidate to evaluate the intensity of the sensation using the following 7 point scale:

| Score | Sensation |
| --- | --- |
| 0 | No sensation |
| 0.5 | Barely perceptible sensation |
| 1 | Mild sensation |
| 2 | Slight sensation |
| 3 | Moderate stinging |
| 4 | Severe stinging |
| 5 | Extreme stinging (must wash off immediately) |

Data Collection:

The evaluation scores on skin are taken for water (reference) and the test solution. The rating is recorded for the water (reference) and the test solution.

Data Evaluation:

The skin gentleness index versus water is calculated by subtracting the average rating for water from the average rating for the test solution. The average is calculated over all panelists. Significance of difference between water and test option can be evaluated by using non-parametric statistical analysis at 2-sided 0.05 significance level.

An example of calculation of a skin gentleness index is provided in table X:

TABLE X

| Panelists | Rating water | Rating test option |
| --- | --- | --- |
| 1 | 0.00 | 0.00 |
| 2 | 0.50 | 0.00 |
| 3 | 0.00 | 0.50 |
| 4 | 0.50 | 0.50 |
| 5 | 1.00 | 2.00 |

TABLE X-continued

| Panelists | Rating water | Rating test option |
| --- | --- | --- |
| 6 | 1.00 | 2.00 |
| 7 | 1.00 | 0.00 |
| 8 | 0.00 | 0.50 |
| 9 | 0.00 | 0.50 |
| 10 | 0.50 | 1.00 |
| Averages: | 0.45 (a) | 0.70 (b) |

Skin gentleness index (b) − (a) = 0.25

The basic reference for this type of testing can be found under Frosch, P J and Kligman, A M. A method for appraising the stinging capacity of topically applied substances. Journal of Cosmetic Chemistry 28: 197-209 (1977).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

All w/w concentrations in this document refer to the weight concentration of the compound over the weight concentration of the composition, unless otherwise indicated.

What is claimed is:

1. A wet-wipe comprising a non-woven material, said non-woven material releasably carrying an oil-in-water emulsion composition; said oil-in-water emulsion composition comprising:
   (a) from 0.001% to about 5% w/w of an emollient;
   (b) a surfactant selected from the group consisting of nonionic surfactants, amphoteric surfactants, anionic surfactants, cationic surfactants and combinations thereof, wherein a 1% by weight aqueous solution of said surfactant has a viscosity of less than about 15,000 cps at 25° C.;
   (c) a preservative, wherein said preservative is a paraben-based antimicrobial comprising methylparaben, ethylparaben, and propylparaben, wherein a total concentration of the paraben-based antimicrobial is from about 0.001% to less than 0.3%;
   (d) at least 0.80% of a soothing agent selected from the group consisting of PEG-40 Hydrogenated Castor Oil, PEG-7 Hydrogenated Castor Oil, PEG-50 Hydrogenated Castor Oil, PEG-30 Castor Oil, Sorbitan Isostearate, Isoceteth-20, Sorbeth-30, Sorbitan Monooleate, Coceth-7, PPG-1-PEG-9 Lauryl Glycol Ether, PEG-45 Palm Kernel Glycerides, PEG-20 Almond Glycerides, PEG-24 Hydrogenated Lanolin, PEG-20 Hydrogenated Lanolin, PEG-6 Caprylic/Capric Glycerides, PPG-1 PEG-9 Lauryl Glycol Ether, Lauryl Glucoside Polyglyceryl-2 Dipolyhydroxystearate, Sodium Glutamate, Polyvinylpyrrolidone, N-Vinylcaprolactam, Sodium Coco PG-Dimonium Chloride Phosphate, Linoleamidopropyl PG-Dimonium Chloride Phosphate, Sodium Borageamidopropyl PG-Dimonium Chloride Phosphate, N Linoleamidopropyl PG-Dimonium Chloride Phosphate Dimethicone, Cocamidopropyl PG-Dimonium Chloride Phosphate, Stearamidopropyl PG-Dimonium Chloride Phosphate, Stearamidopropyl PG-Dimonium Chloride Phosphate, Cetyl Alcohol, and combinations thereof; and (e) water;

wherein said oil-in-water emulsion composition has a skin gentleness index of less than about 0.3.

2. The wet-wipe of claim 1 wherein said surfactant is a non-ionic surfactant.

3. The wet-wipe of claim 1 wherein said surfactant is selected from the group consisting of Alkylpolylglucosides, Sodium Trideceth-3 Carboxylate, Bis-PEG/PPG-16/16 PEG/PPG-16/16 Dimethicone, Polysorbate 20 and combinations thereof.

4. The wet-wipe of claim 1 wherein said oil-in-water emulsion composition comprises from about 50% to about 800% of the weight of said wet-wipe.

5. The wet-wipe of claim 1 wherein said non-woven material comprises fibers comprising a material selected from the group consisting of polyolefin, polyester, cellulose, rayon, polyamides, polyesteramide, polyvinyl alcohols, and combinations thereof.

6. The wet-wipe of claim 1 wherein said emollient is a mixture of Cyclopentasiloxane and dimethiconol; said surfactant is an Alkylpolyglucoside; said soothing agent is PEG40 Hydrogenated Castor Oil; and said rheology modifier is selected from the group consisting of: a blend of sucrose palmitate, glyceryl stearate, glyceryl stearate citrate, mannan, and xanthan gum; sodium acryloyldimethyl taurate copolymers; Acrylate homopolymers; Acrylamide Crosspolymers; Galactoarabinan; xanthan gum and combinations thereof.

7. The wet-wipe of claim 1 wherein said emollient comprises Cyclopentasiloxane and Dimethiconol; said surfactant is an Sodium Trideceth-3 Carboxylate; said soothing agent is PEG-40 Hydrogenated Castor Oil; said rheology modifier selected from the group consisting of: a blend of sucrose palmitate, glyceryl stearate, glyceryl stearate citrate, mannan, xanthan gum; sodium acryloyldimethyl taurate copolymers; Acrylate homopolymers; Acrylamide Crosspolymers; Galactoarabinan; xantham gum and combinations thereof; and said adjunct ingredient comprises glycerine.

8. The wet-wipe of claim 1 wherein said emollient comprises dimethicone and a C12-15-alkylbenzoate; said surfactant is an Bis-PEG/PPG-16/16 PEG/PPG-16-16 Dimethicone and polysorbate 20; said soothing agent is PEG-40 Hydrogenated Castor Oil; and said rheology modifier comprises a blend of hydroxyethyl acrylate/sodium acryloyldimethyltaurate copolymer, squalane and polysorbate 60.

9. An article of commerce comprising a container housing one or more of said wet-wipes of claim 1.

10. A method of cleaning the skin comprising the step of contacting said skin with said wet-wipes of claim 1.

11. The wet-wipe of claim 1 wherein said emollient has a solubility parameter of between 5 and 12 and said emulsion composition has a surface tension lower than 35 mN/m.

12. The wet-wipe of claim 1 wherein said emollient is selected from the group consisting of Dimethicone, Cyclopentasiloxane Dimethiconol, Caprylic/Capric Triglyceride, C12-C15 Alykylbenzoate, and combinations thereof.

13. The wet-wipe of claim 1, wherein the oil-in-water emulsion composition has a pH of from about 5 to about 7.

14. An oil-in-water emulsion composition for wet-wipes comprising:

(a) from 0.001% to about 5% w/w of an emollient;

(b) a surfactant selected from the group consisting of non-ionic surfactant, amphoteric surfactant, anionic surfactant, cationic surfactant and a combinations thereof, wherein a 1% by weight aqueous solution of said surfactant has a viscosity of less than about 15,000 cps at 25° C.;

(c) a preservative, wherein said preservative is a paraben-based antimicrobial comprising methylparaben, ethylparaben and propylparaben, wherein a total concentration of the paraben-based antimicrobial is from about 0.001% to less than 0.3%;

(d) at least 0.8% of a soothing agent selected from the group consisting of PEG-40 Hydrogenated Castor Oil, PEG-7 Hydrogenated Castor Oil, PEG-50 Hydrogenated Castor Oil, PEG-30 Castor Oil, Sorbitan Isostearate, Isoceteth-20, Sorbeth-30, Sorbitan Monooleate, Coceth-7, PPG-1-PEG-9 Lauryl Glycol Ether, PEG-45 Palm Kernel Glycerides, PEG-20 Almond Glycerides, PEG-24 Hydrogenated Lanolin, PEG-20 Hydrogenated Lanolin, PEG-6 Caprylic/Capric Glycerides, PPG-1 PEG-9 Lauryl Glycol Ether, Lauryl Glucoside Polyglyceryl-2 Dipolyhydroxystearate, Sodium Glutamate, Polyvinylpyrrolidone, N-Vinylcaprolactam, Sodium Coco PG-Dimonium Chloride Phosphate, Linoleamidopropyl PG-Dimonium Chloride Phosphate, Sodium Borageamidopropyl PG-Dimonium Chloride Phosphate, N Linoleamidopropyl PG-Dimonium Chloride Phosphate Dimethicone, Cocamidopropyl PG-Dimonium Chloride Phosphate, Stearamidopropyl PG-Dimonium Chloride Phosphate, Stearamidopropyl PG-Dimonium Chloride Phosphate, Cetyl Alcohol, and combinations thereof;

(e) water;

(f) a rheology modifier; and (g) an adjunct;

wherein said oil-in-water emulsion composition has a skin gentleness index of less than about 0.3.

15. The wet-wipe of claim 14 wherein a 1% by weight aqueous solution of said rheology modifier has a surface tension below about 80 mN/m at 25'Celsius.

16. The wet-wipe of claim 14 wherein said emollient comprises a mixture of Caprylic/Capric Triglyceride and Bis-PEG/PPG-16/16 PEG/PPG-16/16 Dimethicone; said surfactant is an Alkylpolyglucoside; said soothing agent is PEG40 Hydrogenated Castor Oil; and said rheology modifier selected from the group consisting of: a blend of sucrose palmitate, glyceryl stearate, glyceryl stearate citrate, mannan, and xanthan gum; sodium acryloyldimethyl taurate copolymers; Acrylate homopolymers; Acrylamide Crosspolymers; Galactoarabinan; xantham gum and combinations thereof.

17. The oil-in-water emulsion composition of claim 14 wherein said emollient is silicon based.

18. A wet-wipe comprising the oil-in-water emulsion composition of claim 14.

19. The wet-wipe of claim 14 wherein said rheology modifier is selected from the group consisting of: a blend of sucrose palmitate, glyceryl stearate, glyceryl stearate citrate, mannan, and xanthan gum; sodium acryloyldimethyl taurate copolymers; Acrylate homopolymers; Acrylamide Crosspolymers; Galactoarabinan; xanthan gum and combinations thereof.

* * * * *